US010254214B1

(12) United States Patent
Griffith et al.

(10) Patent No.: US 10,254,214 B1
(45) Date of Patent: Apr. 9, 2019

(54) SYSTEMS, DEVICES, AND METHODS FOR COMBINED WAFER AND PHOTOMASK INSPECTION

(71) Applicant: Nanotronics Imaging, Inc., Cuyahoga Falls, OH (US)

(72) Inventors: Randolph E. Griffith, Hollister, CA (US); Jeff Andresen, Gilroy, CA (US); Scott Pozzi-Loyola, Watsonville, CA (US); Michael Moskie, San Jose, CA (US); Steve Scranton, San Martin, CA (US); Alejandro S. Jaime, Hollister, CA (US); John B. Putman, Celebration, FL (US)

(73) Assignee: Nanotronics Imaging, Inc., Cuyahoga Falls, OH (US)

( * ) Notice: Subject to any disclaimer, the term of this patent is extended or adjusted under 35 U.S.C. 154(b) by 0 days.

(21) Appl. No.: 15/899,456

(22) Filed: Feb. 20, 2018

(51) Int. Cl.
*G01N 21/01* (2006.01)
*G01N 21/88* (2006.01)
*G01N 21/956* (2006.01)
*G01N 21/95* (2006.01)

(52) U.S. Cl.
CPC ......... *G01N 21/01* (2013.01); *G01N 21/8806* (2013.01); *G01N 21/9501* (2013.01); *G01N 21/956* (2013.01); *G01N 2021/0106* (2013.01); *G01N 2021/95676* (2013.01)

(58) Field of Classification Search
CPC ............... G01N 21/01; G01N 21/8806; G01N 21/9501; G01N 21/956; G01N 2021/0106; G01N 2021/95676

USPC ...................... 356/237.1–237.6, 239.1–239.8
See application file for complete search history.

(56) References Cited

U.S. PATENT DOCUMENTS

| 7,508,504 | B2 | 5/2009 | Jin et al. | |
|---|---|---|---|---|
| 2004/0012776 | A1* | 1/2004 | Bae | G01N 21/9501 356/237.4 |
| 2012/0140060 | A1* | 6/2012 | Tsuchiya | G01N 21/95607 348/126 |
| 2012/0235036 | A1* | 9/2012 | Hatakeyama | G01N 23/2251 250/310 |
| 2018/0005864 | A1 | 1/2018 | Rudmann et al. | |
| 2018/0019147 | A1 | 1/2018 | Boyea et al. | |
| 2018/0025931 | A1 | 1/2018 | Nemani et al. | |

* cited by examiner

*Primary Examiner* — Tri T Ton
(74) *Attorney, Agent, or Firm* — Byrne Poh LLP (57) ABSTRACT

Systems, devices, and methods for combined wafer and photomask inspection are provided. In some embodiments, chucks are provided, the chucks comprising: a removable insert, wherein the removable insert is configured to support a wafer so that an examination surface of the wafer lies within a focal range when the chuck is in a first configuration, wherein the removable insert is inserted into the chuck in the first configuration; and a first structure forming a recess that has a depth sufficient to support a photomask so that an examination surface of the photomask lies within the focal range when the chuck is in a second configuration, wherein the removable insert is not inserted into the chuck in the second configuration.

12 Claims, 11 Drawing Sheets

FIG. 9

SYSTEMS, DEVICES, AND METHODS FOR COMBINED WAFER AND PHOTOMASK INSPECTION

TECHNICAL FIELD

The present disclosure relates to mechanisms for combined inspection of wafers and wafer photomasks.

BACKGROUND

Inspecting wafers and photomasks (collectively, specimens) for defects and other characteristics is important for managing the semiconductor manufacturing process. Since the overall semiconductor manufacturing process involves hundreds of steps, it is critical to detect defects on the wafer or photomask early in the manufacturing process. To help detect defects that occur during the manufacturing process (as well as other specimen characteristics), manufacturers often employ automatic microscopic inspection systems.

Current microscopic inspection systems used by manufacturers are dedicated to either analyzing wafers for defects or analyzing photomasks for defects. Since wafers and photomasks have different dimensions and properties, separate microscopic inspection systems are used to accommodate these different dimensions and properties. For example, a stage included in an inspection system has a chuck attached to it that is specifically sized to hold either a wafer or photomask. Since a photomask is thicker than a wafer, existing chucks cannot be used for both photomasks and wafers. Unfortunately, buying and maintaining separate microscopic inspection systems can be very costly.

In a current wafer inspection system, in order to inspect both a wafer and a photomask using the same system, at the very least, a chuck that holds a specimen (e.g., a wafer or a photomask) to be examined would have to be changed each time a different type of specimen was placed on the chuck (e.g., switching from a wafer to a photomask or from a photomask to a wafer). Manually changing chucks between wafer and photomask inspections is disadvantageous, because additional adjustments (e.g., refocusing the objectives, reattaching vacuum connections, aligning automatic systems, and providing suitable safety features) are usually required when changing chucks. In particular, constantly switching between chucks can damage components of the inspection system (including the chuck itself), reduce the accuracy of specimen analyses, and introduce environmental contaminants into the inspection system. Also, changing out a chuck typically requires particularized knowledge, which operators of a microscopic inspection system may not have. Reducing the adjustments and calibrations that are necessary when switching between a wafer and photomask would reduce damage to the microscopic inspection system, minimize error, and allow for a repeatable, quality controlled microscopic inspection system.

Accordingly, it is desirable to provide a new mechanism for the combined inspection of wafers and photomasks.

SUMMARY

Systems, devices, and methods for combined wafer and photomask inspection are provided. In some embodiments, chucks are provided, the chucks comprising: a removable insert, wherein the removable insert is configured to support a wafer so that an examination surface of the wafer lies within a focal range when the chuck is in a first configuration, wherein the removable insert is inserted into the chuck in the first configuration; and a first structure forming a recess that has a depth sufficient to support a photomask so that an examination surface of the photomask lies within the focal range when the chuck is in a second configuration, wherein the removable insert is not inserted into the chuck in the second configuration.

In some embodiments, automatic inspection systems are provided, the systems comprising: an end effector that is coupled to a robotic system; a microscopic inspection station; a controller that controls one or more components of the automatic inspection system; and a chuck coupled to a stage comprising: a removable insert, wherein the removable insert is configured to support a wafer so that an examination surface of the wafer lies within a focal range when the chuck is in a first configuration, wherein the removable insert is inserted into the chuck in the first configuration; and a first structure forming a recess that has a depth sufficient to support a photomask so that an examination surface of the photomask lies within the focal range when the chuck is in a second configuration, wherein the removable insert is not inserted into the chuck in the second configuration.

DETAILED DESCRIPTION

In accordance with some embodiments of the disclosed subject matter, mechanisms (which can include systems, methods, devices, apparatuses, etc.) for automated microscopic inspection of wafers and photomasks are provided. Microscopic inspection (sometimes referred to as examination) refers to scanning, imaging, analyzing, measuring and any other suitable review of a specimen using a microscope.

In some embodiments, microscopic inspection can be used with a single or several wafer material types including opaque, transparent or semi-transparent. Further, in some embodiments, microscopic inspection can be configured to analyze one or all of substrate, epi, patterned and diced wafers, or individual devices (on the wafer).

Although the following description refers to 300 mm wafers and 150 mm photomasks, in some embodiments, the mechanisms described herein can be used to inspect any sized wafer and/or any sized photomask.

According to some embodiments of the disclosed subject matter, microscopic inspection can operate in two modes: a first mode for inspecting a wafer; and a second mode for inspecting a photomask. As described herein, in some embodiments, microscopic inspection can be configured to operate in a first mode for inspecting a wafer when a removable wafer insert is inserted into a chuck and to operate in a second mode for inspecting a photomask when the removable wafer insert is removed from the chuck.

Figure 1A:
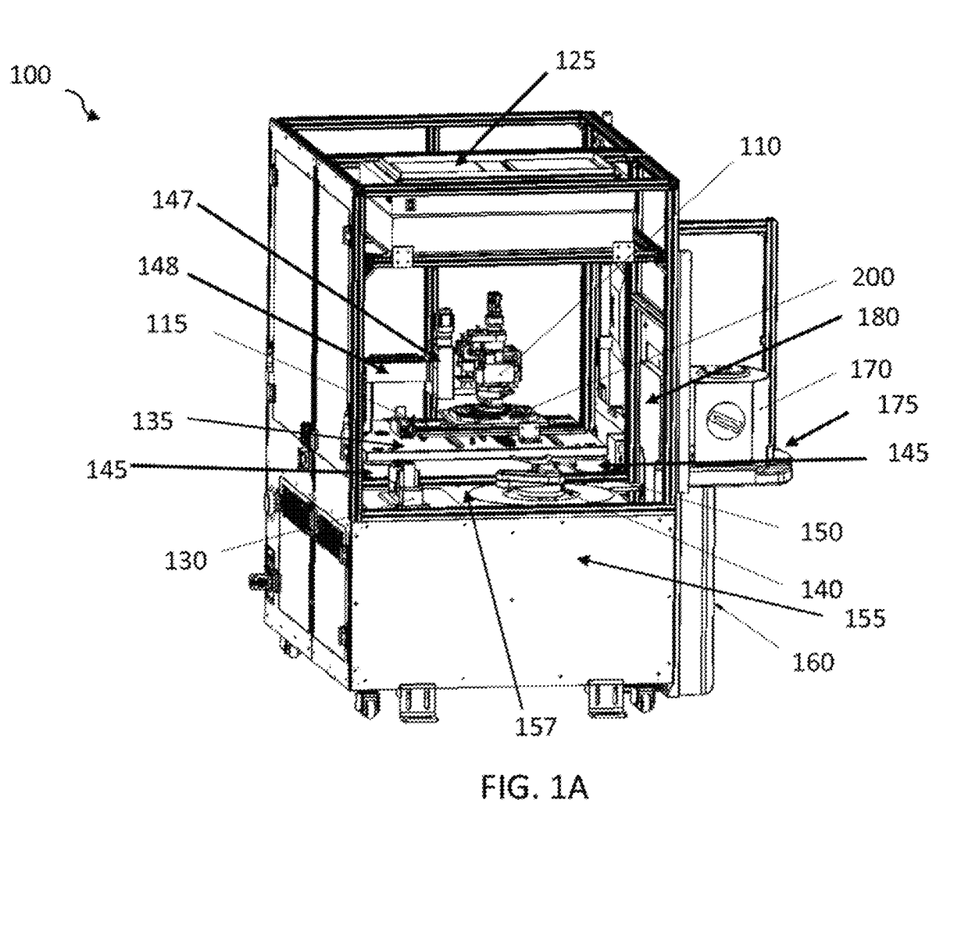
FIG. 1A shows a front perspective view of an example of an inspection system in accordance with some embodiments of the disclosed subject matter.
Figure 1B:
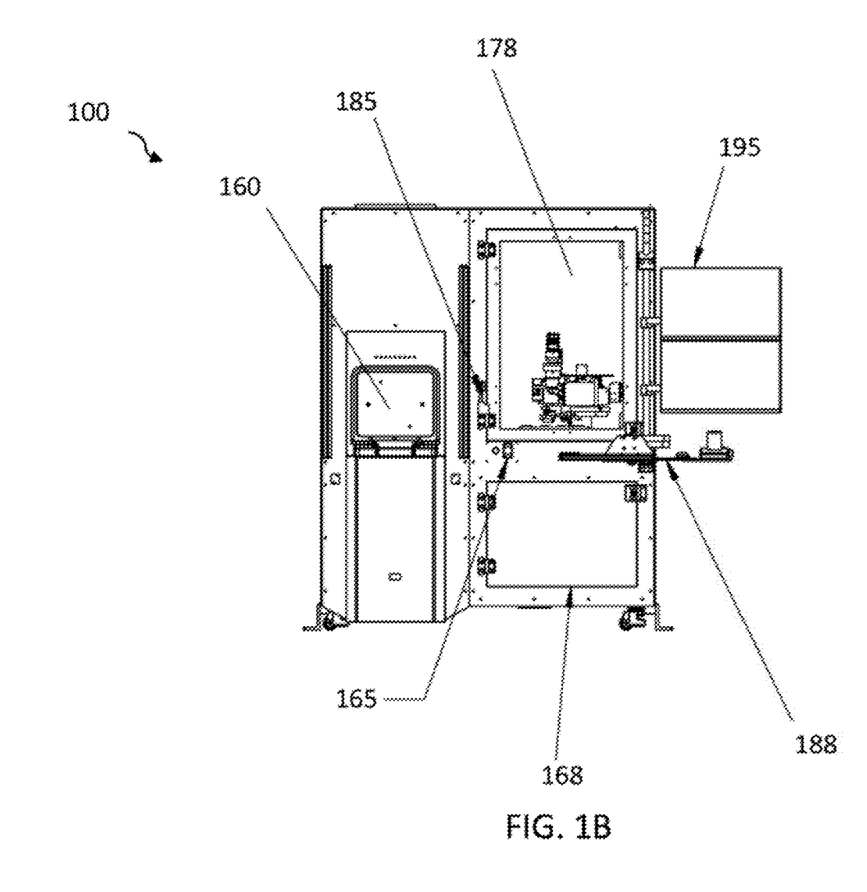
FIG. 1B shows a side view of an example of an inspection system in accordance with some embodiments of the disclosed subject matter.

FIGS. 1A (front perspective view) and 1B (side view) illustrate an example inspection system 100 according to some embodiments of the disclosed subject matter. At a high level, the basic components of inspection system 100, according to some embodiments, include an automated microscopic examination station 110, a pre-aligner 130, a robotic wafer handling system 140, a load port apparatus 160, and electronics comprising hardware, software, and/or firmware.

In some embodiments, many of the components of inspection system 100, as shown in FIGS. 1A and 1B, can be enclosed within a cabinet housing made from aluminum, steel, plastic, glass, and/or any other suitable material for providing a micro clean environment within the cabinet housing. The cabinet housing can include one or more access doors that provide access to the internal components of inspection system 100. Further, in some embodiments, an air filtration system 125 for providing a micro clean environment within the cabinet can be placed, for example at the top of the cabinet housing. The cabinet housing can include one or more storage regions, located for example at the bottom of the cabinet housing, for housing a robotic wafer handling system and/or a vacuum source. The cabinet housing can also include one or more platforms for mounting the various components of inspection system 100. In some embodiments, inspection system 100 can also be partially or completely open. In some embodiments, a variety of cabinet housing configurations can be used in accordance with some embodiments of the disclosed subject matter.

As shown in FIGS. 1A and 1B, inspection system 100 includes an automated microscopic examination station 110. In some embodiments, automated microscopic examination station 110 comprises oculars, such as an ocular and/or a camera, a light source, an illuminator, one or more objective lenses, a stage 115 and a chuck 200 coupled to the stage 115.

Automated microscopic examination station 110 can use any suitable type of microscope. For example, in some embodiments, the microscope can be an optical microscope, an electron microscope, a scanning probe microscope or any other suitable microscope. More particularly, automated microscopic examination station 110 can be implemented using the nSpec® optical microscope available from Nanotronics Imaging, Inc. of Cuyahoga Falls, Ohio Microscopic examination station 110 can be configured to inspect a specimen (e.g., a wafer or a photomask) and automatically report on selected characteristics of the specimen.

According to some embodiments, automated microscopic examination station 110 can include, one or more objectives. The objectives can have different magnification powers and/or be configured to operate with brightfield/darkfield microscopy, atomic force microscopy (AFM), differential interference contrast (DIC) microscopy, and/or any other suitable form of microscopy. The objective and/or microscopy technique used to inspect a specimen can be controlled by software, hardware, and/or firmware in some embodiments. In some embodiments, any suitable settings and/or adjustments to the components of automated microscopic examination station 110 can be controlled by software, hardware and/or firmware.

In some embodiments, an XY translation stage can be used for stage 115. The XY translation stage can be driven by stepper, servo, linear motor, and/or any other suitable mechanism.

In some embodiments, as shown in FIG. 1A, stage 115 and chuck 200 of automated microscopic examination station 110 can be mounted to isolation platform 135 located above a base platform 157 of the cabinet housing. For example, isolation platform 135 can be secured to the bottom frame of the cabinet housing. More particularly, in some embodiments, isolation platform 135, can be bolted into air pads 145, or any other suitable isolation mechanisms for fastening isolation platform 135 to the bottom frame of the cabinet housing. Air pads 145 can help reduce vibration (e.g., from fans of other components in inspection system 100) to a specimen on chuck 200 during examination.

In some embodiments, an extended arm 148 can be mounted to isolation platform 135. A motorized Z-column 147 coupled to the optics portion of the microscopic examination station 110 can be mounted to extended arm 148. In some embodiments, the optics portion can be configured to move up and down on motorized Z-column 147. Mounting the entire microscopic examination station 110 to isolation platform above the base platform of the cabinet housing can help to distribute the weight of the microscopic examination station 110 evenly and minimize vibration to the microscopic examination station 110 during examination.

Pre-aligner 130 can be a stand-alone unit or integrated into the robot wafer handling system. In some embodiments, as shown in FIG. 1A, pre-aligner 130 is a stand-alone unit that is mounted with bolts or other suitable fasteners to a base platform of the cabinet. Pre-aligner 130 can be used for orienting and/or centering a wafer or other suitable specimen so that the specimen is properly oriented and centered when it is placed on chuck 200 for examination. In some embodiments, pre-aligner 130 can use an indicator, for example a notch (e.g., on wafers 200 MM or greater) or a flat (e.g., on wafers less than 200 MM) to orient the wafer so that the wafer is placed on the stage with a specific orientation. Pre-aligner 130 can rotate the wafer up to 360 degrees to find the indicator. In some embodiments, pre-aligner 130 can measure center location and orientation of a wafer in a single rotation.

According to some embodiments, when a specimen is received by pre-aligner 130, pre-aligner 130 can be configured to turn on a vacuum to hold the specimen in place during the centering and/or aligning process. The pre-aligner can also be configured to start the alignment and/or centering process only after the vacuum is turned on. When the pre-aligner has completed handling the wafer, the pre-aligner vacuum can be configured to shut off.

Note that, in some embodiments, any suitable pre-aligner can be used with inspection system 100.

Pre-aligner 130 can be configured to support wafers of any suitable size (e.g., 50 mm to 300 mm, and/or any other suitable size). In some embodiments, pre-aligner 130 can also be configured to communicate with the other components of inspection system 100. In some embodiments, communications and operations of pre-aligner 130 can be controlled by software, hardware and/or firmware.

In some embodiments, a robotic wafer handling system for transferring a wafer or other suitable specimen within inspection system 100 can include a base housing, a motor (not shown), a multi-axis extendable arm 140, and an end effector 150. As shown in FIG. 1A, the base of the robotic wafer handling system can be stored in a region 155 below a base platform 157 of the cabinet housing. Multi-axis extendable arm 140 can extend above base platform 157 and can have two ends. One end can be coupled to the base of the robotic wafer handling system and the other end can be coupled to end effector 150. In some embodiments, end effector 150, as shown in FIG. 1A, can be in the shape of a multi-fingered hand. Different types of end effectors can be used with the robotic wafer handling system in some embodiments. For example, in some embodiments, a vacuum end effector can be used that applies vacuum pressure to hold a specimen in place on the end effector. As another example, in some embodiments, an edge grip end-effector can be used that that uses any suitable gripping mechanism to hold the specimen in place on the end effector.

Note that, in some embodiments, multiple end effectors or a dual end effector can be used with inspection system 100 to handle two or more specimens at different locations within inspection system 100.

Note that, in some embodiments, any suitable robotic wafer handling system(s) that includes any suitable multi-axis extendable arm and/or end effector can be used with inspection system 100. In some embodiments, end effector 150 of the robotic wafer handling system can be configured to support any suitable size wafers, such as, for example, 50 mm to 300 mm size wafers. In some embodiments, end effector 150 can be configured to support a photomask. In some embodiments, all settings, communications, and operations of the robotic wafer handling system can be controlled by software, hardware and/or firmware.

In some embodiments, a motor housed in the base of the robotic wafer handling system can control the movement of multi-axis extendable arm 140 and end effector 150. For example, the motor can drive and control multi-axis extendable arm 140 and end effector 150 to select a wafer from a cassette storage and move the wafer to different locations within inspection system 100. In some embodiments, end effector 150 can transfer the wafer from the cassette storage to pre-aligner 130 for alignment, from pre-aligner 130 to chuck 200 for examination, and from chuck 200 back to the cassette storage when examination of the wafer is complete.

In some embodiments, inspection system 100 can include a load port apparatus 160 (as shown in FIGS. 1A and 1B) for transferring wafers and/or other suitable specimens between a storage container and inspection system 100. In some embodiments, load port apparatus 160 can be mounted to the outside of the cabinet housing of inspection system 100. Load port apparatus 160 can include a door 180 that provides access to the inside of inspection system 100. In some embodiments, the door can be configured to slide up and down to provide access to the inside of inspection system 100. Load port apparatus 160 also includes a platform 175 for holding a wafer carrier or other suitable specimen carrier.

In some embodiments, a front opening unified pod (FOUP) 170 can be placed on platform 175 of load port apparatus 160. FOUP 170 can include various coupling plates, pins and holes for securing the FOUP to the load port platform. In some embodiments, FOUP 170 can be a plastic enclosure designed to cleanly and securely hold wafers and to allow wafers to be transferred from FOUP 170 to microscopic inspection system 100 for processing. FOUP 170 can include a side door that can be opened to provide access to wafers inside. In some embodiments, for example, FOUP 170 can hold 25 wafers. In some embodiments, a side door of FOUP 170 can be aligned with load port door 180 to create a seal. Load port apparatus 160 can be configured to draw the mated doors of load port apparatus 160 and FOUP 170 down and up. In one position (e.g., the down position), the wafers in FOUP 170 can be exposed to the inside of the inspection system 100 and provide access to end effector 150 to select a wafer. In a second position (e.g., the up position), both FOUP 170 and inspection system 100 are sealed off from each other, restricting access between them. FOUP 170 can include sensors to detect and communicate with inspection system 100 when wafers are present in FOUP 170.

In some embodiments, end effector 150 can include one or more sensors for mapping the inside of FOUP 170 to detect each location in FOUP 170 that stores a wafer.

FIG. 1B, shows a side view of inspection system 100 and some of its components, according to some embodiments of the disclosed subject matter. In particular, FIG. 1B shows an emergency power off (EPO) switch 165 coupled to the outside of inspection system 100 that allows an operator to electrically shut down all robotic operations of the robotic wafer handling system, as well as any other electrical operation of inspection system 100, when the switch is activated. In some embodiments, the vacuum remains on to prevent damage to the specimen.

The cabinet housing of inspection system 100, can also include an access door 178 that provides access to components within the inspection system. Access door 178 is coupled to an interlock hinge 185, or any other suitable switch, that is designed to disable any moving component within inspection system 100 when access door 178 is open. In some embodiments, any access door to the inspection system 100 can include a switching mechanism that is designed to disable any moving component within inspection system 100 when the door is opened.

In some embodiments, the electronics controlling inspection system 100 can be located in a separate compartment of the cabinet housing, for example, below automated microscopic examination station 110. In some such embodiments, electronics controlling inspection system 100 can be accessed using access door 168. In some embodiments, the electronics can include any suitable hardware, software, and/or firmware for controlling the operation, communication, and settings of the components of the inspection system 100, as described herein. In some embodiments, inspection system 100 includes software and/or hardware to provide motion control, specimen handling, safety interlocks, and analysis of wafers and photomasks. Hardware can include, for example, computers, microprocessors, microcontrollers one or more EPROMS, EEPROMs, application specific integrated circuits (ASICs) in addition to other hardware elements. In some embodiments, individual components within inspection system 100 can include their own software, firmware, and/or hardware to control the individual components and communicate with other components in inspection system 100.

Inspection system 100 can also include one or more display monitors 195 coupled to the outside of inspection system 100. Display monitors 195 can display images captured by microscopic examination station 110. An adjustable swingarm 188 for placing input devices (e.g., a keyboard, mouse or joystick) for controlling the electronics can also be coupled to inspection system 100, and located, for example, below display monitors 195.

Figure 2A:
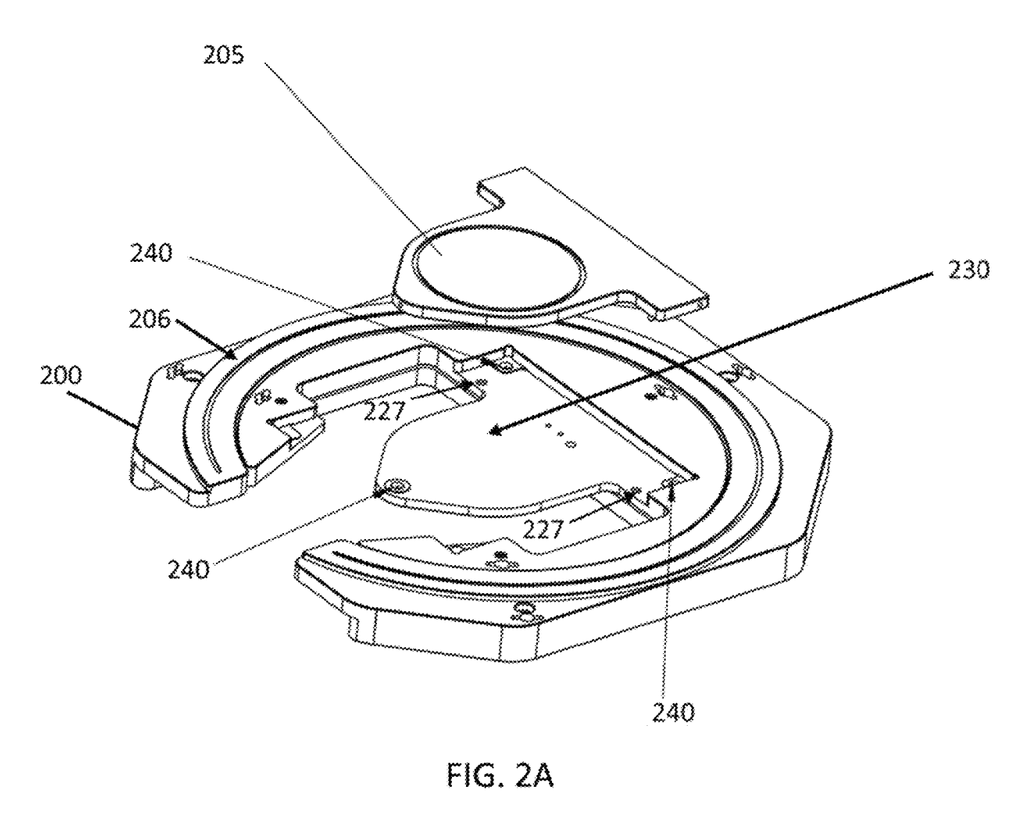
FIG. 2A shows a top perspective view of an example of a chuck in accordance with some embodiments of the disclosed subject matter.
Figure 2B:
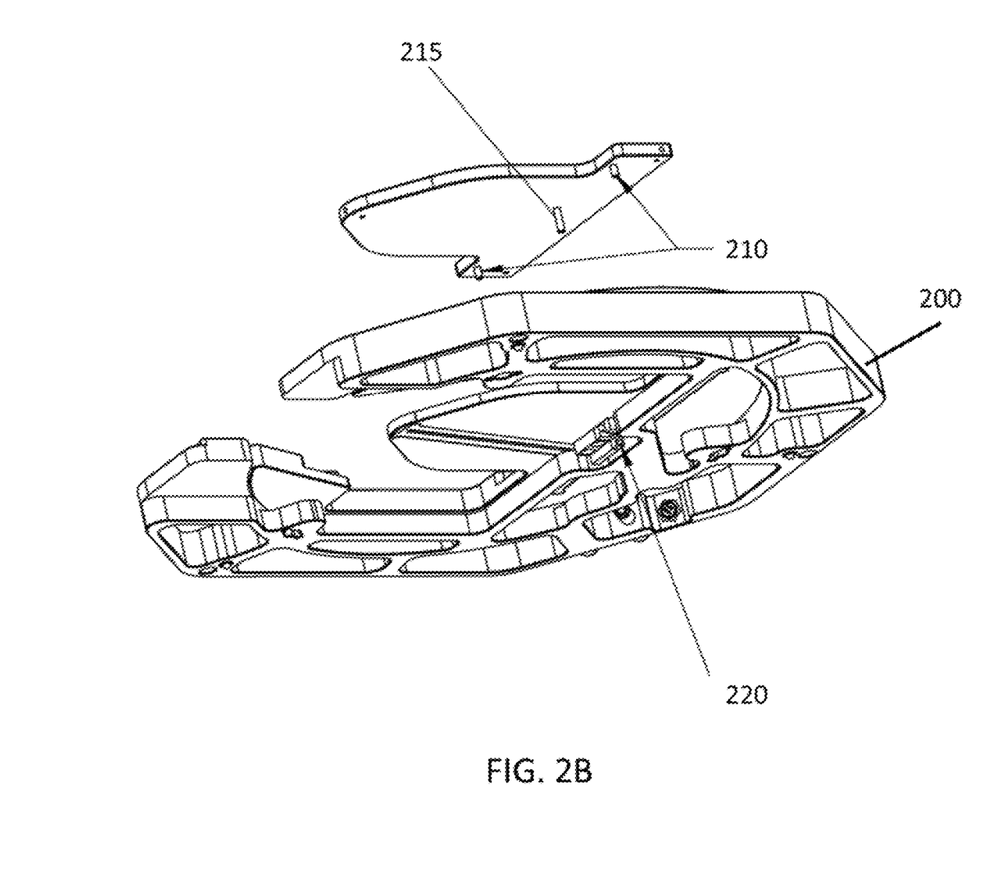
FIG. 2B shows a bottom perspective view of an example of a chuck in accordance with some embodiments of the disclosed subject matter.
Figure 3A:
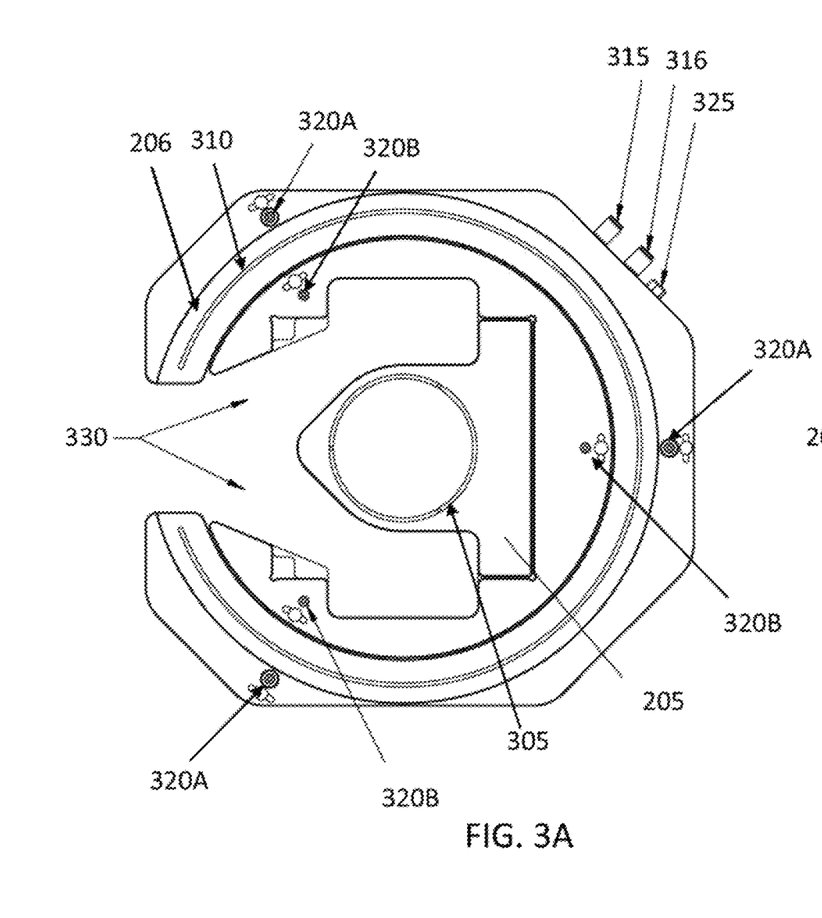
FIG. 3A shows a top view of an example of a chuck in accordance with some embodiments of the disclosed subject matter.
Figure 3B:
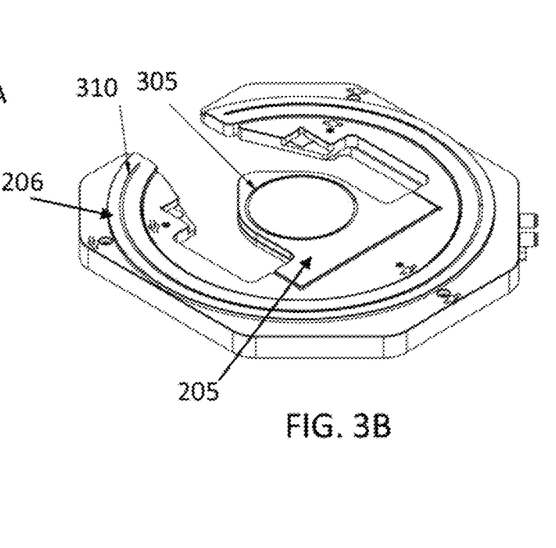
FIG. 3B shows a top perspective view of an example of a chuck in accordance with some embodiments of the disclosed subject matter.

FIG. 2A (top view) and FIG. 2B (bottom view), show the general configuration of an embodiment of a chuck 200 and a removable wafer insert 205 in accordance with some embodiments of the disclosed subject matter. Chuck 200 can be formed from aluminum, steel and/or any other suitable material(s). Chuck 200 is designed to support both a photomask and a wafer at different times. In some embodiments, chuck 200 is C-shaped with a relief area 330 (as shown in FIGS. 3A and 3B) designed to allow access to a two-fingered end effector 150 for placing or removing a specimen on to or off of the chuck. Chuck 200 can be mounted to the top surface of stage 115 of microscopic examination station 110, using standard fasteners like spring screws or leveling screws.

In some embodiments, chuck 200 can include a removeable wafer insert 205 designed to support a wafer and to allow the insert to be removed from the base of chuck 200. In some embodiments, chuck 200 can be in a first configuration when removable wafer insert 205 is inserted in chuck 200, and, in the first configuration, chuck 200 can be used to support a wafer for inspection by inspection system 100. In some embodiments, chuck 200 can be in a second configuration when removable wafer insert 205 is not inserted in chuck 200, and, in the second configuration, chuck 200 can be used to support a photomask for inspection by inspection system 100.

Removable wafer insert 205 can include locating pins 210 (as shown in FIG. 2B) that engage holes 227 (as shown in FIG. 2A) that align removable wafer insert 205 to a corresponding mate 230 located within a recess of chuck 200. In some embodiments, corresponding mate 230 can include one or more vacuum cups 240. Vacuum cups 240 can be connected to a vacuum source (not shown) and designed to provide a vacuum interface to secure removable wafer insert 205 to chuck 200 when inspection system 100 is used to inspect a wafer, and/or to secure a photomask (e.g., photomask 405, as shown in and described below in connection with FIGS. 4A and 4B) to chuck 200 when inspection system 100 is used to inspect photomask. In some embodiments, the vacuum source will not turn on until all the access doors to the cabinet of inspection system 100 are closed. Note that, in some embodiments, any other suitable fastening mechanism(s) can be used to secure removable wafer insert 205 to chuck 200.

Removable wafer insert 205 can also include an interlocking safety mechanism like an interlocking pin 215 (as shown in FIG. 2B). Interlocking pin 215 can activate a sensor 220, located on chuck 200, for sensing when removable wafer insert 205 is inserted into or removed from chuck 200. Sensor 220 can be any suitable sensor for detecting the presence of pin 215, such as an optical sensor or an electro-mechanical switch. The output of sensor 220 can be connected to the electronics of inspection system 100 via interlock sensor connector 325 (as shown in FIGS. 3A and 3B) and can be configured to enable certain electrical operations (e.g., the electrical operations of the robotic wafer handling system) when removable wafer insert 205 is inserted into chuck 200 and to disable certain electrical operations (e.g., the electrical operations of the robotic wafer handling system) when removable wafer insert 205 is removed from chuck 200.

Figure 8A:
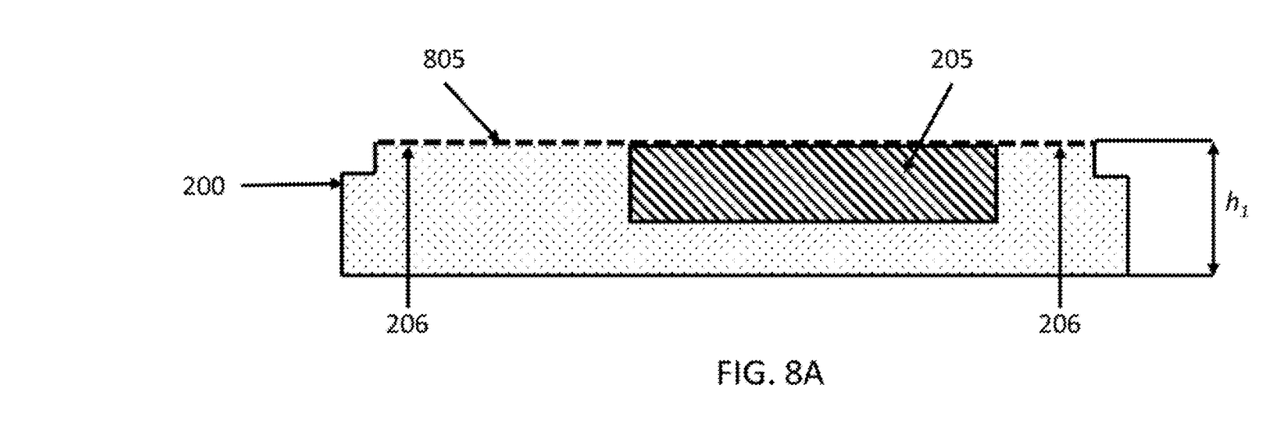
FIG. 8A shows an example illustration of a chuck with an insert inserted and a wafer resting on the chuck and the insert, and height profile of each, in accordance with some embodiments of the disclosed subject matter.

The thickness of removable wafer insert 205, in some embodiments, can be thick enough to cause the top surface of insert 205 to be at the same level and flat with respect to outer wafer support surface 206. FIG. 8A shows a simple cross-sectional illustration of a chuck 200, a removable insert 205, and a wafer 805. As illustrated, the top of insert 205 can be flat and level with outer wafer support surface 206 so that a wafer 805 can lie flat across insert 205 and surface 206.

Figure 8B:
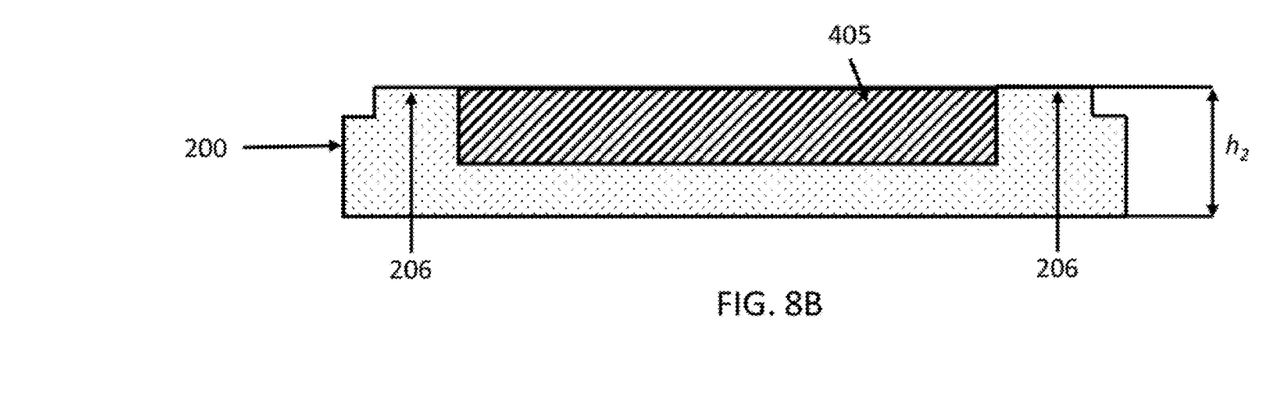
FIG. 8B shows an example illustration of a chuck without an insert inserted and a photomask sitting in a recess in the chuck, and height profile of each, in accordance with some embodiments of the disclosed subject matter.

FIG. 8B shows a simple cross-sectional illustration of a chuck 200 and a photomask 405. As illustrated, the top of photomask 405 can be at the same level and flat with respect to outer wafer support surface 206 in some embodiments. Thus, in such embodiments, the height ($h_2$) at the top of the photomask with respect to the bottom of the chuck can be different than the height ($h_1$) at the top of a wafer when sitting on surface 206 and insert 205 (as shown in FIG. 8A) by an amount equal to the thickness of a wafer. For example, in some embodiments, $h_1$ and $h_2$ can be different but both be within a focal range (which can be any suitable thickness, such as 1 mm thick, in some embodiments) of automated microscopic examination station 110 (FIG. 1A).

In some embodiments, rather than being at the same level and flat with respect to outer wafer support surface 206, the top of photomask 405 can be slightly higher than outer wafer support surface 206 (e.g., by an amount around or equal to the thickness of a wafer) so that the height ($h_2$) at the top of the photomask with respect to the bottom of the chuck is substantially the same as the height ($h_1$) at the top of a wafer when sitting on surface 206 and insert 205 (as shown in FIG. 8A).

In some embodiments, removable wafer insert 205 and chuck 200 can include multiple vacuum channels (e.g., vacuum ring 305 and outer vacuum channel 310 as shown in FIGS. 3A and 3B) for providing vacuum pressure at various locations on chuck 200 to hold a specimen firmly in place during examination. The vacuum configuration for chuck 200 can provide any suitable vacuum pressure for the type of specimen being examined.

Figure 4A:
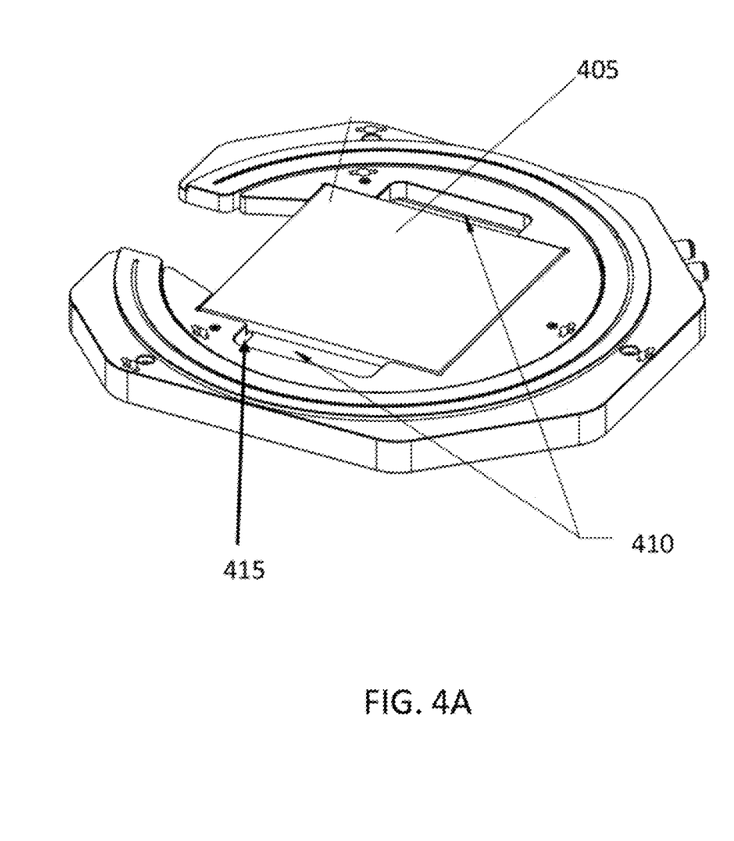
FIG. 4A shows a top perspective view of an example of a chuck holding a photomask in accordance with some embodiments of the disclosed subject matter.
Figure 4B:
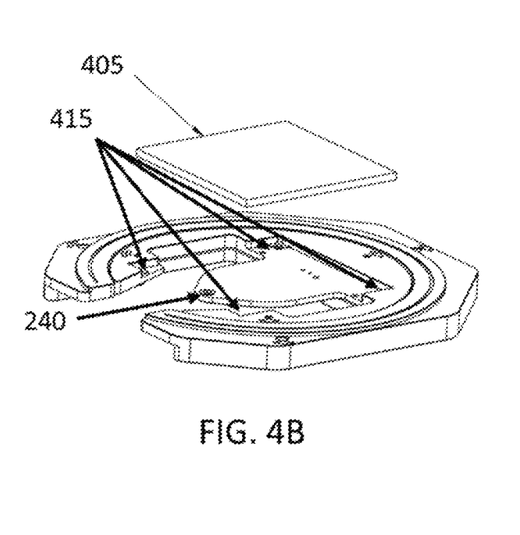
FIG. 4B shows a top perspective view of an example of a chuck with a photomask about to be placed in it in accordance with some embodiments of the disclosed subject matter.

As shown in FIGS. 3A and 3B, in some embodiments, vacuum ring 305 can be located on removable wafer insert 205 and outer vacuum channel 310 can be located in outer wafer support surface 206. The vacuum can be supplied via vacuum valves 315 and 316, which, in some embodiments, can be located along the outer edge of chuck 200 so as not to interfere with the vacuum supply when removable wafer insert 205 is removed from chuck 200. Vacuum valves 315 and 316 can be coupled (e.g., via a hose) with a vacuum source, which can be located in some embodiments within inspection system 100. In some embodiments, both vacuum valves 315 and 316 can be open when a wafer is placed on chuck 200 and provide vacuum flow to both vacuum ring 305 and outer vacuum channel 310. In some embodiments, when a photomask, which can have a smaller surface area than a wafer, is placed on chuck 200, then only vacuum valve 316 can be opened to provide sufficient vacuum support to vacuum cups 240 for providing vacuum support to a photomask. For example, when photomask 405 (as shown in FIGS. 4A and 4B) is placed on chuck 200, the vacuum supply to outer vacuum channel 310 can remain turned off, because photomask 405 does not extend to vacuum channel 310. In some embodiments, any suitable vacuum configurations can be used with chuck 200. In some embodiments, the source vacuum can be regulated to 60 KPa, which can be applied for both wafers and photomasks.

Figure 9:
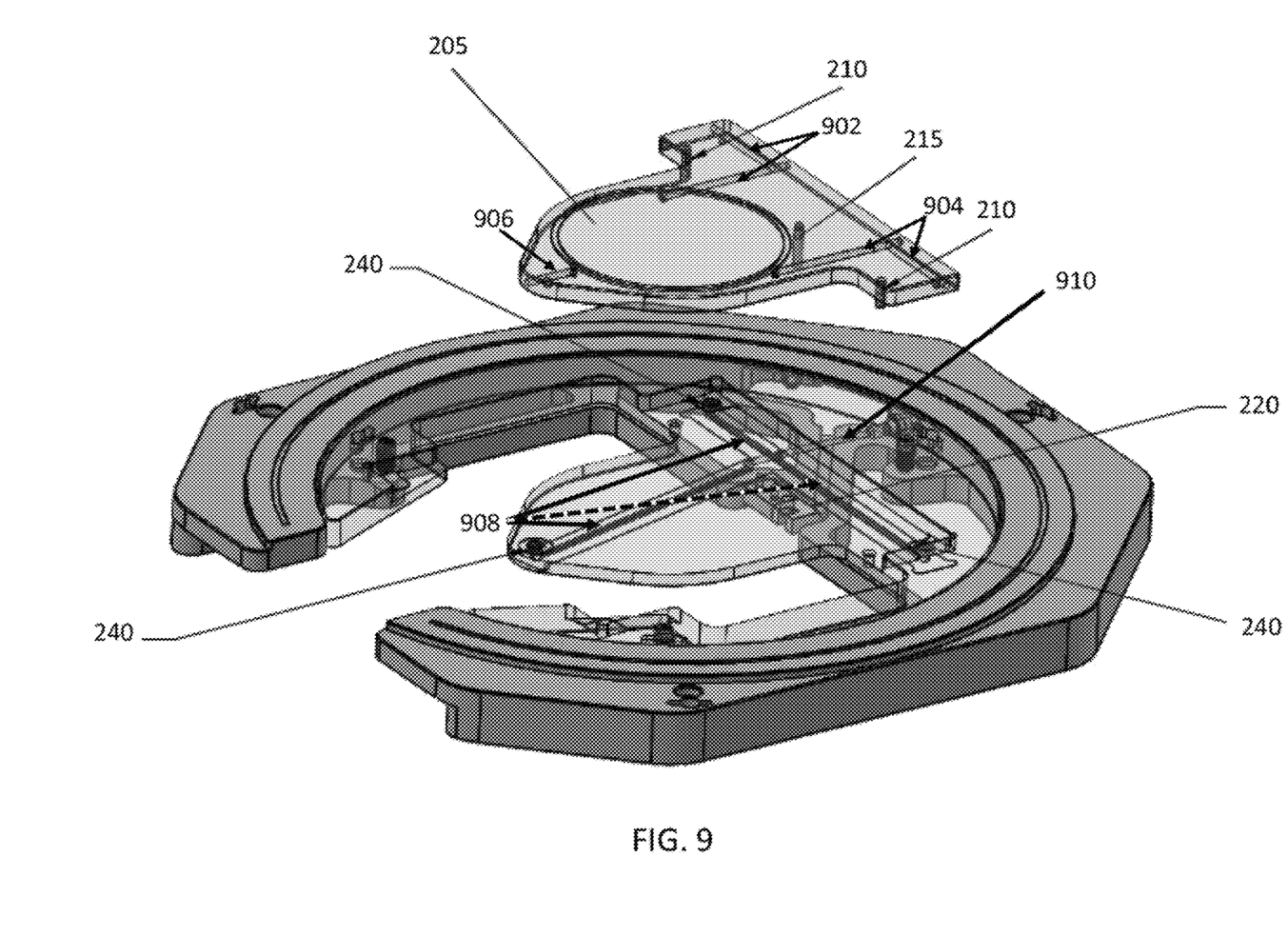
FIG. 9 shows a top perspective view of an example of a chuck and an insert showing vacuum channels within the chuck and the insert in accordance with some embodiments of the disclosed subject matter.

FIG. 9 shows an illustration of an example of vacuum channels 902, 904, 906, 908, and 910 for connecting valves 315 and 316 (FIGS. 3A and 3B) to vacuum ring 305, vacuum channel 310 and vacuum cups 240.

Chuck 200 can also include any suitable number of leveling screws 320A and 320B (e.g., 3 point leveling screws, and/or any other suitable number and/or type of leveling screws) to enable an operator to ensure that outer wafer support surface 206 of the chuck is level and flat. More particularly, one set of leveling screws 320A can be used to level outer wafer support surface 206 with respect to the focal range (which can be any suitable thickness, such as 1mm thick, in some embodiments) of automated microscopic examination station 110 (FIG. 1A) by repositioning the chuck with respect to a lower structure to which it is attached. Another set of leveling screws 320B can be used to level and adjust the height of removable wafer insert 205 when it is inserted into chuck 200 by repositioning corresponding mate 230 with respect to the remainder of the chuck.

In some embodiments, chuck 200 can be designed to support wafers of different sizes and thicknesses by using wafer inserts of different thicknesses. For example, a first removable wafer insert 205 can have a first thickness (e.g., 151700 µm when used with a chuck having a recess that is 152000 µm deep with respect to a point within the focal range of automated microscopic examination station 110) for a first wafer thickness (e.g., 300 µm) and a second removable wafer insert 205 can have a second thickness (e.g., 151840 µm when used with the chuck having a recess that is 152000 µm deep with respect to the point within the focal range of automated microscopic examination station 110) for a second wafer thickness (e.g., 160 µm) so that the combined thickness (e.g., 152000 µm) of the insert and the wafer put the examination surface of the wafer within the focal range of automated microscopic examination station 110 (FIG. 1A).

Other features, like the configuration of vacuum channels and the placement of leveling screws, can be suitably designed based on the size of the wafers.

FIG. 4A (a top perspective view of example chuck 200 when photomask 405 is on the chuck) and FIG. 4B (a top perspective view of example chuck 200 before photomask 405 is placed on the chuck) show an illustration of chuck 200 in which removable wafer insert 205 is removed to allow for photomask 405 to be placed on chuck 200. As shown, chuck 200 can include four corner shelves 415 that create a recess in the chuck (which can be at least as thick as the thickness of photomask 405 in some embodiments) for placing the surface of photomask 405 within the same microscopic inspection focal range (which can be any suitable thickness, such as 1 mm, in some embodiments) as a wafer when the photomask is positioned on the chuck, as described above in connection with FIGS. 8A and 8B.

Chuck 200 can also include first and second relief areas 410 for placing or removing photomask 405 on to or off of chuck 200. In some embodiments, keeping the surface of a wafer and the surface of a photomask in the same focal range (which can be any suitable thickness, such as 1 mm, in some embodiments) eliminates the need to change the focus of the microscopic examination station 110 when switching between inspecting a wafer and inspecting a photomask.

As shown in FIG. 4B, in some embodiments, vacuum cup 240 (as described above in connection with FIG. 2A) can provide a vacuum interface for photomask 405 to hold the photomask firmly in place during inspection. FIG. 4B also shows corner shelves 415, which are also designed to provide support to photomask 405.

Figure 5:
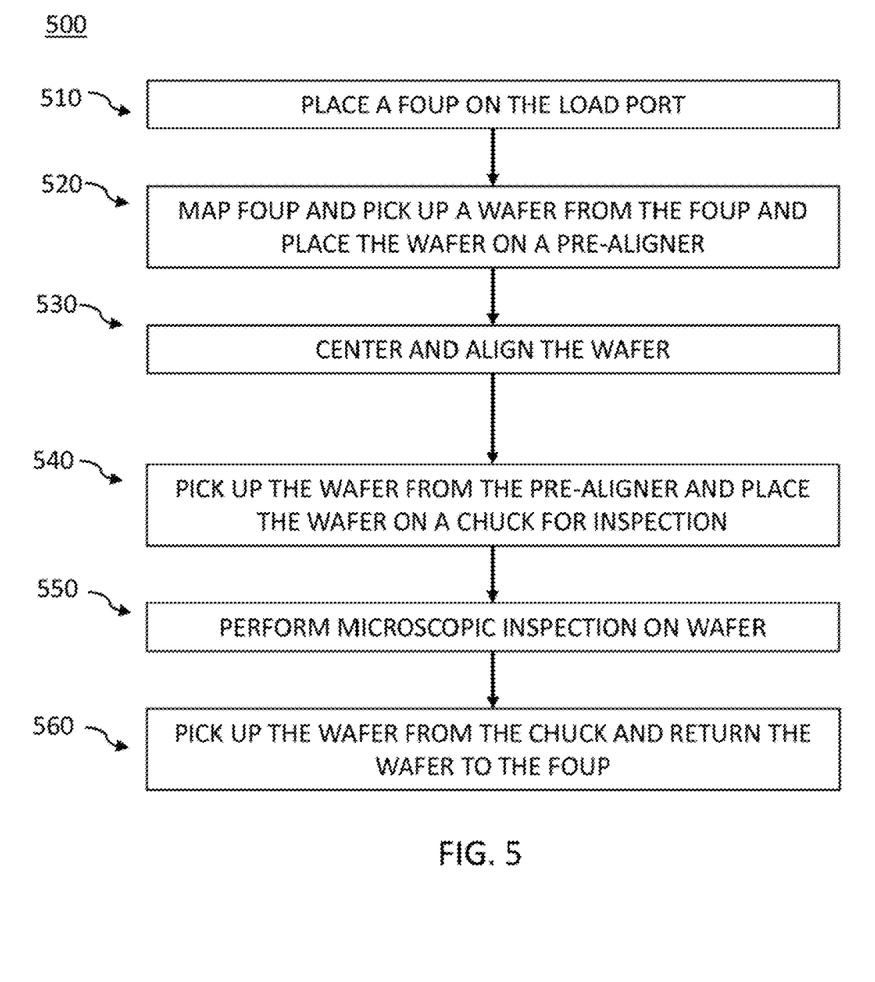
FIG. 5 shows a flow chart of an example of a process for loading a wafer within an inspection system, such as the system illustrated in FIGS. 1A and 1B, in accordance with some embodiments of the disclosed subject matter.

FIG. 5, with further reference to FIGS. 1-4, shows at a high level, a wafer loading operation 500 of inspection system 100, in accordance with some embodiments of the disclosed subject matter. The wafer loading process 500 can use inspection system 100.

At 510, FOUP 170 can be placed on load port apparatus 160, so that the door of FOUP 170 and load port door 180 fasten together in a sealable manner. FOUP 170 and load port door 180 can be lowered together, exposing the wafers in FOUP 170 to the inside of inspection system 100 and providing access to end effector 150 to select a wafer.

At 520, robotic end effector 150 can map the FOUP to determine how many wafers are in the FOUP and where they are located. In some embodiments, robotic end effector 150 can map the FOUP using any suitable sensors associated with robotic end effector 150. End effector 150 can then pick up a wafer from FOUP 170, and transfer the wafer to pre-aligner 130. In some embodiments, a vacuum can be turned on when or after a wafer is picked up for keeping the wafer on end effector 150 and the vacuum can be turned off after the wafer is transferred to pre-aligner 130.

At 530, pre-aligner 130 can center and/or orient a wafer (e.g., by using a notch or a flat). In some embodiment, pre-aligner 130 can turn on a vacuum when or after it receives the wafer before it starts any wafer centering and/or aligning procedure, and turn off the vacuum when or after the wafer centering and/or aligning procedure is completed.

At 540, end-effector 150 can pick up a wafer from pre-aligner 130 and place the wafer on chuck 200 for inspection by automated microscopic examination station 110. Vacuum pressure for chuck 200 can be turned on when or after the wafer is placed on chuck 200.

At 550, process 500 can perform microscopic inspection on the wafer using any suitable technique or combination of techniques. For example, as described above in connection with FIGS. 1A and 1B, process 500 can use an automated microscopic examining station that includes any suitable type of microscope (e.g., an optical microscope, an electron scanning microscope, a scanning probe microscope, and/or any other suitable type of microscope) to obtain any suitable information during inspection of the wafer.

At 560, when or after inspection of the wafer is completed, vacuum pressure can be turned off and end effector 150 can retrieve the wafer from chuck 200 and return the wafer to FOUP 170.

In some embodiments, once all the wafers are inspected, load port door 180 and FOUP 170 can be raised together, sealing off the access between FOUP 170 and inspection system 100. In some embodiments, vacuum pressure can be applied when a wafer is present on end effector 150, and the vacuum for the end effector can be turned off when the wafer is transferred to another component of inspection system 100.

Note that, in some embodiments, wafers can be manually loaded into inspection system 100 and placed directly on chuck 200 without using FOUP 170.

Additionally, note that, in some embodiments, process 500 can be performed in response to determining that removable wafer insert 205 (as shown in and described above in connection with FIGS. 2A and 2B) has been inserted in chuck 200. For example, in some embodiments, process 500 can be performed in response to determining that interlocking pin 215 of removable wafer insert 205 has activated sensor 220 of chuck 200, as described above in connection with FIGS. 2A and 2B.

Figure 6:
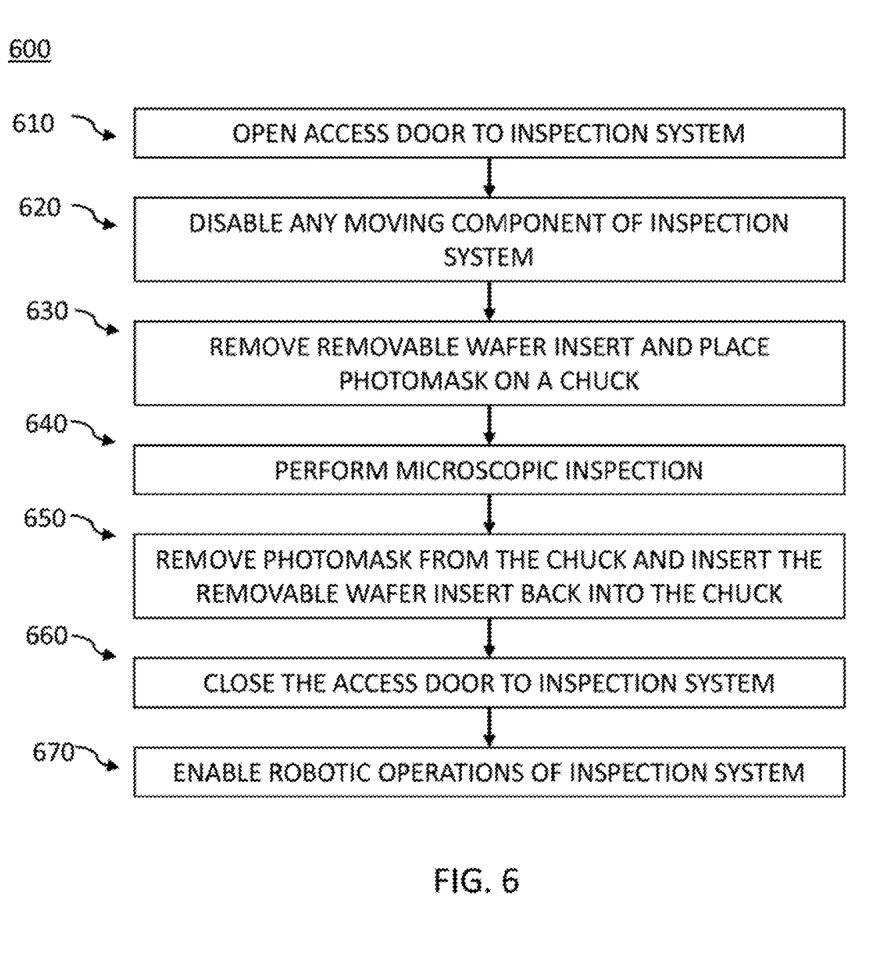
FIG. 6 shows a flow chart of an example of a process for loading a photomask within an inspection system, such as the system illustrated in FIGS. 1A and 1B, in accordance with some embodiments of the disclosed subject matter.

FIG. 6, with further reference to FIGS. 1-4, shows at a high level, a photomask loading operation 600 of inspection system 100, in accordance with some embodiments of the disclosed subject matter. Photomask loading process 600 can use inspection system 100.

At 610, access door 178 can be opened (as shown in FIG. 2). This door can be opened in any suitable manner in some embodiments. For example, this door can be opened manually by an operator or automatically by an actuator in some embodiments.

At 620, in some embodiments, interlock hinge 185 can be activated in response to detecting that access door 178 has been opened. In some such embodiments, process 600 can disable any moving component within inspection system 100, including disabling end effector 150.

At 630, removable wafer insert 205 (as shown in FIG. 2) can be removed and a photomask can be recessed into chuck 200. Insert 205 can be removed in any suitable manner, such as manually by an operator or using an automated mechanism. Photomask can be recessed into chuck 200 in any suitable manner, such as manually by an operator or using an automated mechanism.

At 640, microscopic examination station 110 can inspect the photomask. In some embodiments, microscopic examination station 110 can use any suitable parameters and techniques for inspecting the photomask. For example, in some embodiments, microscopic examination station 110 can use the same or a different focus and objective as was used to inspect a wafer, as described above in connection with FIG. 5. As another example, in some embodiments, microscopic examination station 110 can use a different microscopic technique (e.g., using AFM microscopy) than a technique used to inspect a wafer.

At 650, after inspection of the photomask, the photomask can be removed from chuck 200 and removable wafer insert 205 can be inserted into chuck 200. Photomask can be removed from chuck 200 in any suitable manner, such as manually by an operator or using an automated mechanism. Insert 205 can be inserted in any suitable manner, such as manually by an operator or using an automated mechanism.

At 660, access door 178 can be closed when or after removable wafer insert 205 is inserted into chuck 200. Access door 178 can be closed in any suitable manner, such as manually by an operator or using an automated mechanism.

At 670, the robotic wafer handling system of inspection system 100 can be enabled, as described above in connection with FIG. 5.

Note that, in some embodiments, process 600 can be performed in response to determining that removable wafer insert 205 (as shown in and described above in connection with FIGS. 2A and 2B) is not inserted in chuck 200. For example, in some embodiments, process 600 can be performed in response to determining that interlocking pin 215 of removable wafer insert 205 has not activated sensor 220, as described above in connection with FIGS. 2A and 2B.

Additionally, note that, in some embodiments a photomask can also be automatically loaded into inspection system 100, similar to the techniques used for automatically loading wafers into the inspection system. For example, in some embodiments, a specially designed photomask storage container can be loaded onto load port apparatus 160. The front cover of the photomask storage container and load port door 180 can be lowered, exposing the photomasks inside the photomask storage container to the inside of inspection system 100. The photomask storage container and/or end effector 150 can be designed to sense the presence of a photomask and communicate with the control system of inspection system 100 to perform operations appropriate for photomask inspection. The photomask storage container can be designed to include a designated area for storing removable wafer insert 205. Before any photomask is loaded into inspection system 100, end effector 150 can be configured to remove removable wafer insert 205 from chuck 200 and place it in a designated area in the photomask storage container. Once removable wafer insert 205 has been removed, end effector 150 can select a photomask from the photomask storage container and transfer it to chuck 200 for inspection and/or imaging by microscopic examination station 110. After inspection of the photomask, end effector 150 can pick up the photomask from chuck 200 and return the photomask to the photomask storage container. Once all the photomasks are inspected, end effector 150 can select removable wafer insert 205 and place it back on chuck 200.

Figure 7:
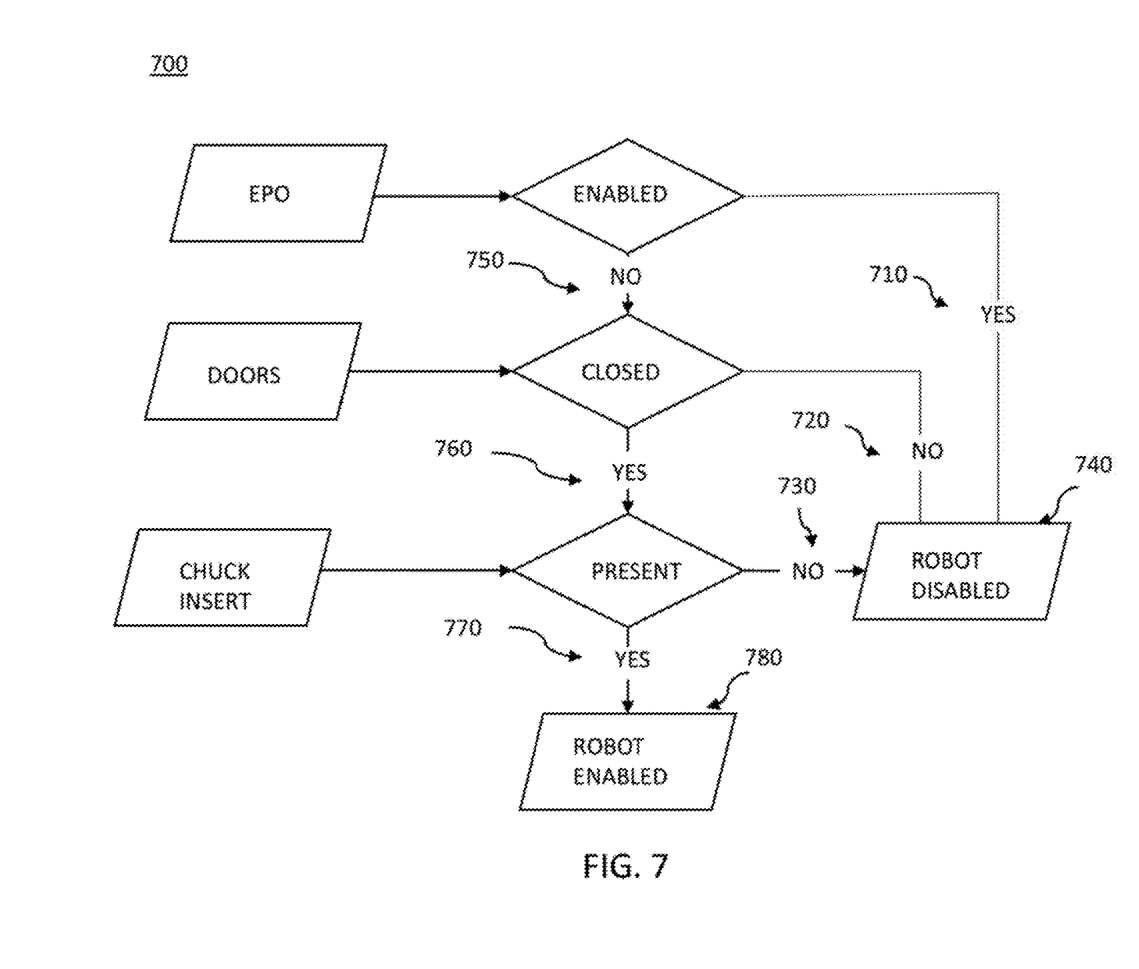
FIG. 7 shows a flow chart of an example of a process for applying interlock logic rules of an inspection system, such as the system illustrated in FIGS. 1A and 1B, in accordance with some embodiments of the disclosed subject matter.

FIG. 7, with further reference to FIGS. 1-4, shows at a high level an example of logic rules 700 for interlocking safety features of an inspection system, such as inspection system 100, in accordance with some embodiments of the disclosed subject matter.

As shown in FIG. 7, according to some embodiments, an inspection system can include three interlocking mechanisms for determining whether a robotic wafer handling system, such as the one shown in and described above in connection with FIG. 5, is to be deactivated or activated.

In some embodiments, the robotic wafer handling system can be disabled at 740 in response to determining that an emergency power off (EPO) button has been activated (at 710), that an access door to the enclosed inspection system 100 is not closed (at 720), or that a wafer insert is not present in chuck 200 (at 730). Note that, in some embodiments, any one of an activated EPO button, not closed access door, and/or lack of removable wafer insert in chuck 200 can disable all robotic operations at 740 by the robotic wafer handling system and/or moveable components within inspection system 100.

Conversely, in some embodiments, the robotic operations of the robotic wafer handling system can be enabled at 780 in response to determining that the following conditions have been met: the EPO button is not enabled (750), access door 178 to inspection system 100 is closed (760), and removable wafer insert 205 is inserted into chuck 200 (770).

The division of when the particular portions of processes 500, 600, and/or 700 are performed can vary, and no division or a different division is within the scope of the subject matter disclosed herein. Note that, in some embodiments, blocks of processes 500, 600, and/or 700 can be performed at any suitable times. It should be understood that at least some of the portions of processes 500, 600, and/or 700 described herein can be performed in any order or sequence not limited to the order and sequence shown in and described in the FIGS. 5, 6, and 7 in some embodiments. Also, some of the portions of processes 500, 600, and/or 700 described herein can be or performed substantially simultaneously where appropriate or in parallel in some embodiments. Additionally or alternatively, some portions of processes 500, 600, and/or 700 can be omitted in some embodiments.

Any one or more of processes 500, 600, and/or 700 can be implemented in any suitable hardware and/or software, for example, one or more EPROMS, EEPROMs, a programmable logic device, application specific integrated circuits (ASICs) or any other hardware or firmware elements.

The automated microscopic inspection system and method that integrates the testing of wafers and photomasks in a single system have been described in detail with specific reference to these illustrated embodiments. It will be apparent, however, that various modifications and changes can be made within the spirit and scope of the disclosure as described in the foregoing specification, and such modifications and changes are to be considered equivalents and part of this disclosure. The scope of the invention is limited only by the claims that follow.

What is claimed is:

1. A chuck, comprising:
   a removable insert, wherein the removable insert is configured to support a wafer so that an examination surface of the wafer lies within a focal range when the chuck is in a first configuration, wherein the removable insert is inserted into the chuck in the first configuration; and
   a first structure forming a recess that has a depth sufficient to support a photomask so that an examination surface of the photomask lies within the focal range when the chuck is in a second configuration, wherein the removable insert is not inserted into the chuck in the second configuration,
   wherein the chuck is coupled to an inspection system, and wherein the chuck includes a sensor that causes operations of the inspection system to be disabled when the removable insert is removed from the chuck.

2. The chuck of claim 1, further comprising:
   a second structure forming at least one vacuum channel configured to engage the wafer when the chuck is in the first configuration and engage the photomask when the chuck is in the second configuration.

3. The chuck of claim 1, wherein the focal range is 1 mm thick.

4. An automatic inspection system, comprising:
   an end effector that is coupled to a robotic system;
   a microscopic inspection station;
   a controller that controls one or more components of the automatic inspection system; and
   a chuck coupled to a stage comprising:
   a removable insert, wherein the removable insert is configured to support a wafer so that an examination surface of the wafer lies within a focal range when the chuck is in a first configuration, wherein the removable insert is inserted into the chuck in the first configuration; and
   a first structure forming a recess that has a depth sufficient to support a photomask so that an examination surface of the photomask lies within the focal range when the chuck is in a second configuration, wherein the removable insert is not inserted into the chuck in the second configuration,
   wherein the automatic inspection system operates in a first operation mode when the chuck is in the first configuration, and wherein the automatic inspection system operates in a second operation mode when the chuck is in the second configuration, and
   wherein the controller is configured to determine that the chuck is in the first configuration when an interlocking pin of the removable wafer insert has activated a sensor of the chuck.

5. The automatic inspection system of claim 4, wherein the automatic inspection system is enclosed.

6. The automatic inspection system of claim 4, wherein the end effector is configured to automatically load a wafer into the automatic inspection system.

7. The automatic inspection system of claim 4, wherein the end effector is configured to automatically load a photomask into the automatic inspection system.

8. The automatic inspection system of claim 4, wherein operations associated with the robotic system are deactivated when the removable insert is not inserted into the chuck.

9. The automatic inspection system of claim 4, wherein operations associated with the robotic system are deactivated when an access door of the automatic inspection system is open.

10. The automatic inspection system of claim 4, wherein operations associated with the robotic system are deactivated when an emergency power off button of the robotic system has been activated.

11. The automatic inspection system of claim 4, wherein the removable wafer insert has one or more locating pins that connect the removable wafer insert to the recess when the chuck is in the first configuration.

12. The automatic inspection system of claim 4, wherein the chuck further comprises: a second structure forming at least one vacuum channel configured to engage the wafer when the chuck is in the first configuration and engage the photomask when the chuck is in the second configuration.

* * * * *